United States Patent [19]

Huynh Dinh et al.

[11] Patent Number: 5,358,937
[45] Date of Patent: Oct. 25, 1994

[54] GLYCOSYL PHOSPHOLIPID DERIVATIVES OF NUCLEOSIDES AND THEIR USE AS MEDICINES

[75] Inventors: Tam Huynh Dinh, Croissy Sur Seine; Catherine Gouyette, Vanves; Jean Igolen, Le Mesnil St-Denis; Robert Fauve, Sevres; Luc Montagnier, Le Plessis Robinson; Yvette Henin; Olivier Schwartz, both of Paris, all of France

[73] Assignee: Institut Pasteur, Paris, France

[21] Appl. No.: 947,991

[22] Filed: Sep. 21, 1992

Related U.S. Application Data

[63] Continuation of Ser. No. 582,966, Nov. 15, 1990, abandoned.

[30] Foreign Application Priority Data

Jan. 30, 1989 [FR] France .................. 89 01134

[51] Int. Cl.$^5$ .................. A61K 31/70; C07H 19/10
[52] U.S. Cl. .................. 514/49; 514/51; 514/934; 536/26.8
[58] Field of Search .................. 536/26.8, 26.2, 34; 514/23, 49, 50, 5, 934

[56] References Cited

FOREIGN PATENT DOCUMENTS

WO89/12062 12/1989 France .

OTHER PUBLICATIONS

Chemical Abstracts: vol. 80; No. 5, n. 23677s, Feb. 4, 1974.
Chemical Abstracts: vol. 98; No. 9, n 72656q, Feb. 23, 1983.
AIDS Research and Human Retroviruses: vol. 4, No. 6, 1988 pp. 449–455.
Chemical Abstract: vol. 86; No. 15 n. 106952c; Apr. 11, 1977.
Chemical Abstracts, vol. 86, No. 15, n106951b, Apr. 11, 1977.
Chemical Abstracts, vol. 90, No. 23, n182936y, Jun. 4, 1979.
Chemical Abstracts, vol. 110, No. 7, n53299a, Feb. 13, 1989.
Chemical Abstracts, vol. 71, No. 9, n36053z, Sep. 1, 1969.
Tetrahedron Letters, vol. 28, No. 31, 1987, Pergamon Press Ltd., pp. 3581–3584.
International Search Report for PCT application PCT/FR90/00073.

Primary Examiner—John W. Rollins
Attorney, Agent, or Firm—Finnegan, Henderson, Farabow, Garrett & Dunner

[57] ABSTRACT

The glycosylphospholipid nucleoside derivatives of the invention are based on the formula:

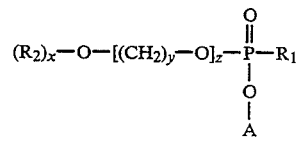

wherein:

$R_1$ is a nucleoside derivative selected from the group consisting of 3'-azidothymidine (AZT); 2', 3'-dideoxythymidine (ddT); and 2'-deoxy-5-fluorouridine (dFU);

$R_2$ is a hexose or pentose sugar, with the exception of glucose when x is 1;

A is a hydrogen atom or an alkyl or alkoxy chain containing from 5 to 20 carbon atoms, said alkyl or alkoxy chain having at its extremity a group selected from the group consisting of a hydrogen atom and an NR'R" group, wherein R' and R" represent hydrogen or an alkyl group of 1 to 4 carbon atoms;

x is a number from 1 to 12;
y is a number from 1 to 4; and
z is 0 or 1; and further wherein:

attachment of said hexose sugar is at position 1 or position 6 of said hexose sugar, and attachment of said pentose sugar is at position 1 or position 5 of said pentose sugar. The derivatives of the invention are useful for producing pharmaceutical compositions having, in particular, anti-vital properties.

18 Claims, No Drawings

GLYCOSYL PHOSPHOLIPID DERIVATIVES OF NUCLEOSIDES AND THEIR USE AS MEDICINES

This application is a continuation, of application Ser. No. 07/582,966 filed Nov. 15, 1990, now abandoned.

The subject of the invention is glycosyl phospholipid derivatives of nucleosides, more particularly thymidine and uridine, possessing in particular antiretroviral properties.

It is known that nucleoside derivatives have been found to be active in the prevention and treatment of the infections caused by retroviruses such as HIV-I and HIV-2.

One of the most useful products is constituted by 3′-azido thymidine (AZT). Other active derivatives of pyrimidine bases are constituted by 2′, 3′-dideoxy thymidine (ddT) and 2′-deoxy-5-fluoro uridine (dFU).

In the application FR 88/07252 dated 31 May 1988, also filed by the present applicants, "Glucosyl phosphotriesters of thymidine derivatives having an activity against retroviruses", glucosylated phosphodiester and phosphotriester derivatives of thymidine possessing in particular an activity toward retroviruses were described.

The further development of these studies has shown that other derivatives of pyrimidine bases possessing a sugar moiety other than glucose, in particular a mannose moiety, possess particularly useful pharmacological properties.

In fact, such derivatives consist, in particular, of lipophilic carriers capable of crossing a cell or vital membrane, nucleotide prodrugs, i.e. the biologically active nucleoside entity as well as targetting vectors directed preferentially towards the macrophages.

Thus, the aim of the invention is to provide phosphodiester and phosphotriester derivatives of thymidine and uridine possessing, in particular, antiretroviral properties.

It also aims to provide a procedure for the preparation of these derivatives.

An additional aim of the invention is to provide medicines containing these derivatives an active ingredient.

The derivatives according to the invention are characterized in that they are glycosylated derivatives corresponding to formula I:

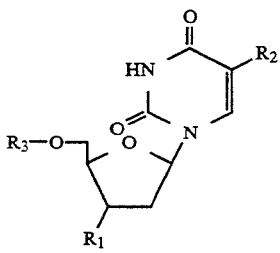
(I)

in which:
$R_3$ represents a group:

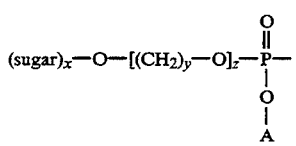

in which:
"sugar" represents a $C_5$ or $C_6$ sugar moiety, D or L, with the exception of glucose when x is equal to 1, the phosphorylated chain substituent being linked to position 1 or position 6 of the sugar moiety to which it is attached, x is a number from 1 to 12 y is a number from 1 to 4 z is equal to 0 or 1, and

A represents a hydrogen atom or alc. group representing a saturated or unsaturated hydrocarbon radical of 5 to 30 carbon atoms, substituted if appropriate, $R_1$ represents a $N_3$ group, a hydrogen atom, an alkyl group with 1 to 4 carbon atoms, a halogen atom, a nitrile group or a hydroxy group, and $R_2$ represents an alkyl group with 1 to 4 a carbon atoms, a halogen atom or a nitrile group.

In the above formula, the sugar moiety is a sugar selected from the D or L, $C_5$ or $C_6$ sugars.

Mention should be made of mannose, galactose, fructose, fucose, the aminohexoses and 2-deoxy glucose in the case of the hexoses and arabinose, xylose, ribose and 2-deoxy ribose in the case of the pentoses.

The mannosylated derivatives are particularly preferred. In addition to membrane transport properties, they enable the nucleoside to be preferentially oriented towards the macrophages which possess receptors with D-mannose molecules.

Since the retroviruses preferentially bind to macrophages and replicate within them, the importance of having available derivatives constituting target vectors for the macrophages can be appreciated. Such a selective orientation of the biologically active molecules in fact enables the side effects of such derivatives or their toxicity towards other types of cells to be reduced.

In one group of derivatives of the invention, x is a number from 2 to 12, these derivatives being then substituted by a disaccharide or an oligosaccharide chain of 3 to 12 sugar moieties, these moieties being identical or different.

Another group of derivatives of the invention contains a single sugar moiety.

The derivatives substituted by mannose are especially preferred.

Particularly useful mannosylated phosphotriester derivatives are phosphorylated at position 6 of the mannose moiety and correspond to the formula II:

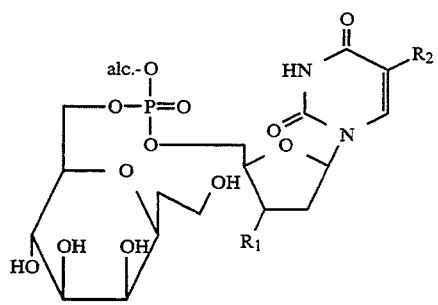

in which alc., $R_1$ and $R_2$ are as defined above.

Another preferred family of phosphotriesters is composed of derivatives phosphorylated at position 1 of the mannose moiety and corresponds to formula III:

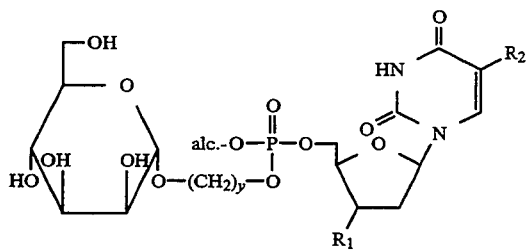

in which $R_1$, $R_2$, y and alc. are as defined above.

In the formulae II and III, the alc. group advantageously represents an alkyl or alkoxy chain containing from 5 to 20 carbon atoms. Where appropriate, this chain is substituted at its extremity by a —$NH_2$, —NHR' or —N(R',R'') group, in which R' and R'', identical or different, represent an alkyl group of 1 to 4 carbon atoms.

Phosphodiesters, precursors of the above phosphotriesters, which are also included in the framework of the invention, advantageously correspond to the formula IV:

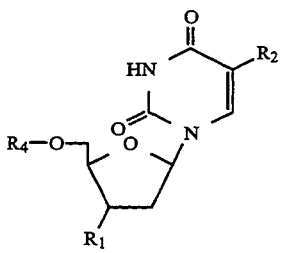

in which
$R_1$ and $R_2$ are as defined above, and
$R_4$ represents a group:

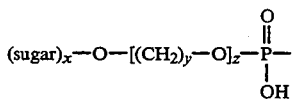

in which the term "sugar", x, y and z are as defined in relation to the formula I.

Preferred nucleoside phosphodiesters contain a mannose moiety substituted at position 6 and correspond more particularly to the formula V:

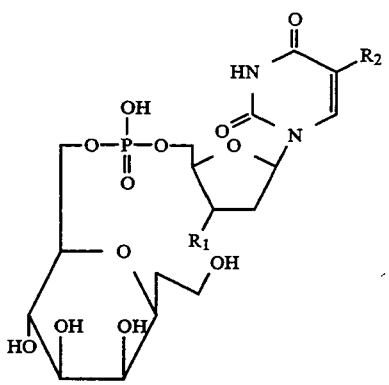

in which $R_1$ and $R_2$ are as defined above.

Other preferred nucleoside phosphodiesters are mannose derivatives phosphorylated at position 1 and correspond to the formula VI:

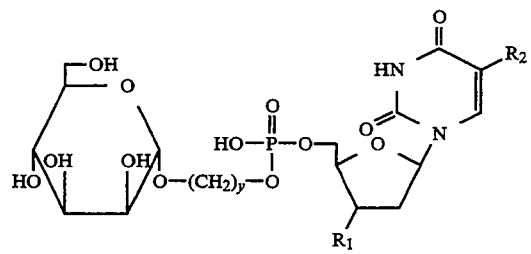

in which $R_1$, $R_2$ and y are as defined above.

Particularly useful derivatives corresponding to the formulae I to VI above are derivatives of 3'-azido thymidine (AZT), 2',3'-dideoxy thymidine (ddT) and 2'-deoxy 5-fluoro uridine (dFU).

The derivatives of formula I of the invention are obtained by implementing the following steps:
  condensation of an oligosaccharide derivative of formula VII:

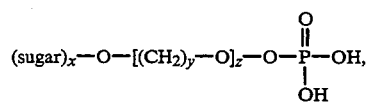

in which
the phosphorylated chain substituent occupies position 1 or position 6 of the sugar moiety to which it is linked, the other hydroxyl radicals of the sugar moiety or moieties being blocked by protecting groups for the hydroxyl radical, these groups being identical or different
x, y and z are as defined above,
with a nucleoside derivative of formula VIII:

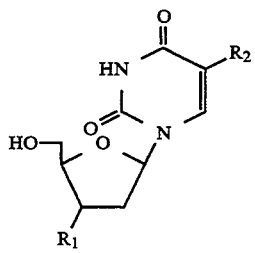

$R_1$ and $R_2$ being as defined above, which leads to a phosphodiester of formula IX in which the sugar moiety or moieties are protected:

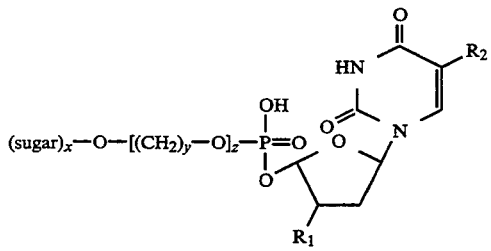

removal of the protecting groups from the sugar moiety or moieties of the phosphodiesters in order to generate the —OH groups followed, if it is desired to prepare a phosphotriester, by the reaction of the phosphodiester with a reagent of formula X. B-alc. in which B represents a group capable of reacting with the —OH group attached to the phosphorus thus linking the alc. radical to the P atom with the formation of a compound BH which will be removed, the phosphotriester formed corresponding to the formula I above in which A represents the alc. group.

The step involving the condensation between the derivatives VII and VIII is advantageously performed at a temperature higher than room temperature, in an organic solvent.

Suitable solvents include pyridine and acetonitrile.

When pyridine is used as reaction solvent, the desired coupling is obtained by working at a temperature between 60° and 80° C., and in particular close to 70° C. The reaction is carried out under an atmosphere of an inert gas such as nitrogen or argon.

It is advantageous to use an excess of the derivative of formula VII relative to the nucleoside of formula VIII. An excess of 1.5 to 2 moles enables the coupling to be carried out under satisfactory conditions.

In order to promote the condensation reaction, an activating compound such as trichloroacetonitrile is added (Cramer F. and Weimann G. (1961) Chem. Ber. 94 996–1007).

The phosphomonoesters used are in the form of the pyridinium, morpholine, tetraethylammonium salt.

The protecting groups are removed prior to the attachment of an alkyl chain.

Among the groups which are suitable for the implementation of the invention mention should be made of acyl groups, in particular acetyl or benzoyl groups or also variously substituted derivatives of these groups.

The removal of these groups is carried out according to the standard techniques of organic chemistry by working under conditions which do not adversely affect the structure of the phosphodiester IX or X nor its substituents.

The acyl groups are removed with the aid of solutions of sodium hydroxide, a NH$_3$/CH$_3$OH mixture or sodium methylate.

For the step involving the attachment of the alc. group, a reagent B-alc. is used in which B is advantageously halide, in particular bromide or iodide, or also a tosylate or a sulfonium salt.

The reaction is advantageously carried out in an organic solvent at a temperature higher than room temperature, in particular between 50° and 100° C. Of the organic solvents which may be used, mention should be made of acetonitrile, dimethylformamide and nitromethane.

The B-alc. reagent is used in an at least 10 fold molar excess with respect to the phosphodiester, which is preferably in the form of a highly reactive salt.

According to another variant of synthesis, a glycoside derivative corresponding to the formula XI:

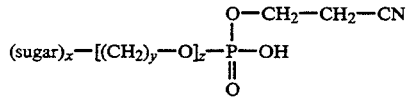

in which x, y and z are as defined in relation to formula I and in which a sugar moiety is substituted at position 6 or position 1 by a cyanoethylphosphate group, this derivative being advantageously in the form of a salt, is made to react with a nucleoside derivative of formula VIII above, then the blocking groups for the hydroxyl functions are removed.

The coupling reaction is advantageously carried out in an organic solvent at ambient temperature in the presence of TPSNT.

The derivative of formula XI is advantageously obtained by reaction of the glycoside or oligosaccharide which it is desired to introduce into the derivative to be synthesized with the cyanoethyl phosphate in the form of a reactive salt.

The anti-retroviral properties of the products of the invention have been demonstrated by studying in vitro more particularly their inhibitory action toward the cytopathogenic effect of the retrovirus and toward the replication of these retroviruses.

In accordance with a feature assuming major importance, these inhibitory actions are produced at doses which are non-toxic for the human T lymphocytes, which makes it possible to use the derivatives of the invention to prepare anti-retroviral compositions.

Thus, another subject of the invention is pharmaceutical compositions characterized in that they contain an efficacious amount of at least one derivative of formula I in combination with a pharmaceutically acceptable vehicle.

The invention relates in particular to the pharmaceutical compositions prepared from mannosylated derivatives.

These compositions are particularly useful for the treatment of AIDS and related diseases.

These compositions are available in forms suitable for administration by the oral, nasal, topical, rectal, vaginal, subcutaneous, intravenous intramuscular or intradermal route.

The compositions to be administered by the oral route include lozenges, tablets, granules, aqueous or non-aqueous solutions or suspensions. Suppositories are used for administration by the rectal route and creams or foams for the vaginal route.

The formulations used for administration by the parenteral route are advantageously composed of sterile or non-aqueous solutions or suspensions.

In order to illustrate the invention, examples of the preparation of thymidine derivatives and the results of pharmacological assays showing the activity of these derivatives are reported below.

EXAMPLE 1

Preparation of the AZT Derivatives of Formula

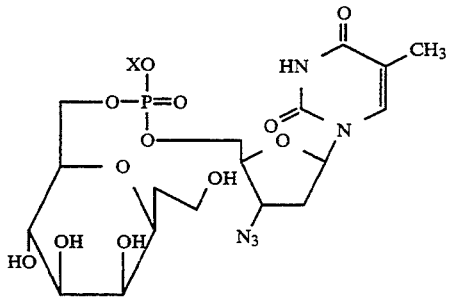

in which X represents a hydrogen atom or a hexadecyl chain.

This synthesis is carried out starting from D-mannose 6-phosphate and comprises the following five steps:
1. Blocking of the —OH groups of D-mannose 6-phosphate
2. Condensation of the protected derivative with 3'-azido thymidine
3. Deprotection of the —OH groups of the mannose moiety
4. Exchange of the pyridinium salt for the tetrabutylammonium salt, and
5. Attachment of a hexadecyl chain to the free—OH group of the phosphate moiety, leading to a phosphotriester.

These steps were carried out as follows:

1: Blocking of the —OH groups of D-mannose 6-phosphate (1) and preparation of the pyridinium salt of 1, 2, 3, 4-tetra-O-acetyl D-mannose 6-phosphate (2).

1 g (3.29 mmoles) of the sodium salt of D-mannose 6-phosphate (1) and 3.6 ml of distilled acetic anhydride (42.3 mmoles) in 4 ml of anhydrous pyridine are stirred for 16 h at room temperature. A white precipitate forms. The course of the reaction is checked by thin layer chromatography (TLC) ($CH_2Cl_2$: $CH_3OH$: $H_2O$ 60/35/5. Rf. of starting material : O ; Rf acetylated product: 0.53.

The precipitate is filtered off and the filtrate is cooled. About 30 ml of ice are added slowly in order to hydrolyse the excess anhydride. The hydrolysis is allowed to continue for 30 min, then the mixture is evaporated to dryness in a vacuum and then coevaporated several times with toluene in order to remove all traces of pyridine. The residue is then taken up in water and the aqueous phase is washed several times with dichloromethane. The volume of the aqueous phase is then reduced before being passed through a column of Dowex 50 WX8 $H^{+R}$ resin, exchanged beforehand in the pyridinium form.

The column effluent is checked by means of TLC and the appropriate fractions are lyophilized: m=1.203 g; yield=63%.

2: Condensation and preparation of the pyridinium salt of 1,2,3,4 tetra-O-acetyl 6-mannosyl 5'-(3'-azido) thymidinylphosphate (3).

100 mg (0.375 mmole) of 3'-azido thymidine (4) and 330 mg (0.375×1.5 mmoles) of 1,2,3,4 tetra-O-acetyl 6-D-mannose phosphate (2) in the pyridinium form are coevaporated 3 times with anhydrous pyridine (distilled over $CaH_2$, then over para-toluene sulfonic chloride). About 10 ml of anhydrous pyridine and 1.275 ml (0.375×34 excess) of trichloroacetonitrile are added. The mixture is heated at 70° C. with vigorous stirring under an atmosphere of nitrogen overnight The course of the reaction is checked by means of TLC ($CH_2Cl_2$: $CH_3OH$: $H_2O$ 13/5/1). The mixture is evaporated to dryness in a vacuum, then the residue is taken up in a minimum of dichloromethane and the product is precipitated by petroleum ether. The solvent is decanted and the precipitate is chromatographed on a Merck $7734^R$ silica column eluted with dichloromethane gradually enriched in methanol. The compound is eluted with a mixture containing 6% methanol: m=202 mg; yield =71%; Rf=0.62 ($CH_2Cl_2$: $CH_3OH$: $H_2O$ 13/5/1).

3: Deprotection of the —OH groups of the mannose and preparation of the pyridinium salt of 6-D-mannosyl-5'(3'-azido) thymidinyl phosphate (5).

In order to remove the acetyl groups, 202 mg of (3) are reacted with 1% sodium methylate in methanol for 10 min. at room temperature. A slight cloudiness appears. A check is made by means of TLC that the reaction is complete.

The reaction mixture is neutralized by the addition of Dowex 50 WX8 $H^{+R}$ resin. At pH=7, the resin and the precipitate are filtered off and the methanolic phase is evaporated to dryness.

The residue is taken up in a minimum of water and passed through a column of Biogel $P_2^R$ 200/400 mesh eluted with water.

The column effluent is monitored by means of U.V. at 254 nm. After TLC, the fractions containing the desired compound are lyophilized before being repassed through a column of $C18^R$ eluted with water: m=78.5 mg; yield=50%; Rf=0.544 (isopropanol: $NH_4OH$: $H_2O$; 7/1/2).

4: Exchange of the pyridinium salt into the tetrabutylammonium salt (6) (product CT 7626).

A column of Dowex 50 WX8 $H^{+R}$ resin previously equilibrated in the tetrabutylammonium form is prepared by stirring this resin in concentrated tetrabutylammonium hydroxide and washing until the pH of the water washings is neutral.

The 78.5 mg of the product (5) previously obtained are passed through this column eluted with water.

The fractions absorbing at 254 nm are collected and lyophilized: m=98 mg; yield=98%; Rf unchanged; mass FAB m $^-$=508 (without $N(Bu)^+_4$); HPLC retention time 10.489 mn (2/25).

5: Attachment of the hexadecyl chain and preparation of 6-D-mannosyl hexadecyl 5'-(3'-azido)-thymidinyl phosphate (7) (product CT 7627).

70 mg (0.093 mmole) of the diester in the tetrabutylammonium form (6) and 0.528 ml (0.093×18 mmoles) of 1-iodohexadecane (8) are coevaporated in a vacuum with anhydrous acetonitrile. About 10 ml of anhydrous acetonitrile are then added and the mixture is heated at 80° C. for 16 to 20 hours with stirring. The completeness of reaction is checked by means of TLC and the reaction mixture is evaporated to dryness. The residue is then loaded onto a Merck $7734^R$ silica column. The elution is begun with pure dichloromethane in order to remove the excess hexadecane, then the eluant is progressively enriched in methanol.

The fractions containing the phosphotriester are eluted by an eluant containing 6% methanol and evaporated to dryness. Product obtained: m=38 mg; yield=56%; Rf=0.674 (isopropanol: $NH_4OH$: $H_2O$ 7/1/2)=0.71 ($CH_2Cl_2$: $CH_3OH$: $H_2O$ 13/5/1; mass : $FAB^+$=734 (m +1); HPLC: retention time: 21.87 min. (5/95-95); NMR (DMSO-d6): $CH_3$ chain (0.87), $(CH_2)_n$(1.25),$CH_2$—$CH_2$—OP(1.63), $CH_2$—$CH_2$—OP(4.01); mannose-$\alpha$ $H_1$ (4.90), $H_2$(3.58), $H_3$(3.57) $H_4$(3.45), $H_5$(3.72), $H_6$(4.23), $H_{6'}$(4.09); nucleotide $H_6$(7.51 and 7.49 41/59), $CH_3$(1.82); $H_{1'}$(6.14), $H_{2'}$(2.44) $H_{2''}$(2.36), $H_{3'}$(4.46), $H_{4'}$(4.02), $H_{5'5''}$(4.20).

EXAMPLE 2

Preparation of ddT Derivatives of Formula

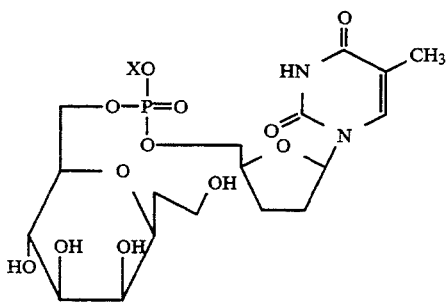

in which X is as defined in example 1.

The procedure is that indicated in example 1. For step 2, 50 mg (0.221 mmole) of ddT (9) and 195 mg (0.221×1.5 mmoles) of acetylated mannose 6-phosphate (2) are treated with 0.75 ml (0.221×34 mmoles) of trichloroacetonitrile in anhydrous pyridine. After chromatography the product obtained: 111 mg of the protected phosphodiester (10); yield=70%; Rf=0.63 ($CH_2Cl_2$: $CH_3OH$: $H_2O$ 13/5/1).

Step 3 is carried out as indicated above.

Starting with 111 mg of the product (10), after passage through Biogel $P_2{}^R$ 200/400 mesh and C18$^R$ 48 mg of deprotected phosphodiester diester (11) are obtained: yield=57%; Rf=0.5 (isopropanol: $NH_4OH$: $H_2O$ 7/1/2).

Step 4, conducted starting from the 48 mg of the phosphodiester (11), leads to 62 mg of phosphodiester in the form of the tetrabutylammonium salt (12) (product CT 7389): yield: 99%; Rf unchanged; mass FAB$^-$=468 (M-1); HPLC retention time: 10.659 (0/25).

The protocol for step 5 is applied to 55 mg (0.075 mmole) of the phosphodiester (12) and 0.44 ml (0.0775×18) of 1-iodohexadecane (8). The product obtained after chromatography: 17 mg of 6-D-mannosyl hexadecyl 5'2', 3'-dideoxy thymidinyl phosphate (13) (product CT 7390): yield=32%; Rf=0.631 (isopropanol: $NH_4OH$: $H_2O$ 7/1/2); Rf=0.82 ($CH_2Cl_2$: $CH_3OH$: $H_2O$ 13/5/1);Mass FAB+m+1=693; HPLC: retention time: 12.933 (50/95).

EXAMPLE 3

Preparation of the dFU Derivatives of Formula

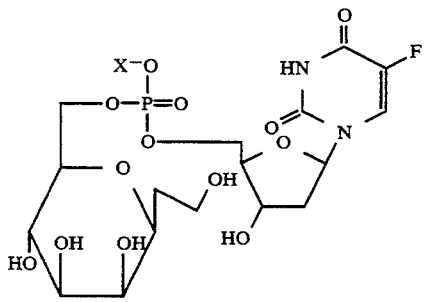

in which x is as defined in example 1.

Recourse is had to the same procedure as that described in example 1.

The step 2 is carried out starting from 250 mg of 2'-deoxy 5-fluoro uridine (1.015 mmole) (14) and 892 mg (1.015×1.5 mmoles) of 1,2,3,4 tetra-O-acetyl 6-D-mannose phosphate (2), treated with 3.55 ml (1.015×34 excess) of trichloroacetonitrile in anhydrous pyridine. After chromatography, 540 mg of the protected phosphodiester (15) are obtained: yield:=72%; Rf:=0.44 ($CH_2Cl_2$: $CH_3OH$: $H_2O$ 13/5/1).

In step 3, starting from the 540 mg of the phosphodiester (15), 200 mg of deprotected phosphodiester (16) are obtained after passage through Biogel$^R$ and C18$^R$: yield=48%; Rf:=0.544 (isopropanol: $NH_4OH$: $H_2O$ 7/1/2)

From the 200 mg of material previously obtained, 238 mg of phosphodiester in the form of the tetrabutylammonium salt (17) (product CT 7088) are obtained in step 4: yield:=92%; Rf:=unchanged; mass FAB$^-$=729 (m-1); HPLC retention time 2 peaks: 2.077 mn, 2.386 mn (5/25).

For stage 5, 218 mg (0.298 mmole) of the diester (17) and 1.689 ml (0.298×18 mmoles) of 1-iodohexadecane (8) are used. 63.4 mg of phosphotriester (18) or CT 7325 are obtained: yield=30%; Rf =0.628 (isopropanol: $NH_4OH$: $H_2O$ 7/1/2)=0.84 ($CH_2Cl_2$: $CH_3OH$: $H_2O$ 13/5/1); mass FAB+=735 (m+NA+); HPLC retention time=12.829 (50/95); NMR (DMSO-$d_6$); $CH_3$ chain (0 85) $(CH_2)_n$(1.24), $CH_2$—$CH_2$—OP (1.58), $CH_2$—$CH_2$—OP(3.99); mannose- α $H_1$(4.90), $H_2$(3.57), $H_3$(3.53), $H_4$(3.41), $H_5$(3.71), $H_6$(4.06), $H_6'$(4.14); nucleotide $H_6$(7.88 and 7.85 45/55), $H_1'$(6.15), $H_2'{}_{2''}$(2.14) $H_3'$(4.24), $H_4'$(3.95), $H_5'{}_{5''}$(4.19).

EXAMPLE 4

Preparation of AZT Derivatives of Formula

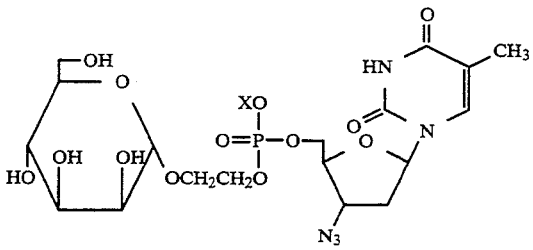

in which X is as defined in example 1.

This synthesis is carried out starting from a derivative of D-mannose, the —OH groups of which are protected with the exception of the anomeric carbon, namely α-1-bromo tetra-O-benzoyl 2,3,4,6-D-mannose (19) and comprises the following steps:

a) Attachment of a benzyloxyethyl chain at position 1
b) Removal of the benzyl group from the chain linked to position 1
c) Attachment of a cyanoethyl phosphate chain
d) Condensation with AZT
e) Removal of the benzoyl groups and the cyanoethyl group
f) Exchange to the tetrabutylammonium salt
g) Attachment of a hexadecyl chain leading to the formation of a phosphotriester.

a) Attachment of a benzyloxyethyl chain at position 1 and preparation of the 1-(2-benzyloxyethyl) 2,3,4,6-tetra-O-benzoyl D-mannose (20).

The following reaction mixture is prepared in a 100 ml round-bottomed flask: 0.71 ml (5 mmoles) of 2-benzyloxyethanol (21) in 15 ml of anhydrous nitromethane and 15 ml of anhydrous toluene. 2.282 g (5×1.266 mmoles) of mercuric bromide $HgBr_2$ and 1.6 g (5×1.266 mmoles) of mercuric cyanide HgCN$_2$ are added as well as 5 g of 4 A molecular sieves. The mixture is stirred for 1 h in the tightly stoppered flask. 3.295 g (5 mmoles) of α-1-bromo 2,3,4,6-tetra-O-benzoyl D-mannose (19) are then added. The reaction mixture is stirred for one hour under nitrogen until the reaction is complete as shown by TLC (ethyl acetate: hexane ½; Rf of starting material=0.38; Rf of expected product: 0.28).

The precipitate is filtered off and the filtrate is diluted with toluene. The organic phase is then washed with ice-cold water, ice-cold saturated sodium bicarbonate and again with ice-cold water. The organic phase is evaporated to dryness after drying over sodium sulfate and filtration.

The oil obtained is chromatographed on a column of Merck 7734$^R$ silica equilibrated with a hexane/10% ethyl acetate mixture, which is gradually enriched in ethyl acetate. The desired product is eluted with a mixture containing 30% ethyl acetate. The product (20) is obtained in the form of a pale yellow oil: m=3.079 g; yield=80%; Rf=0.28 (ethyl acetate: hexane ½).

b) Removal of the benzyl group from the chain at position 1 and preparation of 1-(2-hydroxyethyl) 2,3,4,6-tetra-O-benzoyl D-mannose (22).

The oil previously obtained (20) is dissolved in 60 ml of absolute ethanol and hydrogenolysis is performed in the presence of 50 mg of 10% palladium on charcoal.

The first check by means of TLC is made after a reaction time of one hour (AcOEt: hexane 2/1; Rf of starting material: 0.65; Rf of expected product: 0.44) Ac=CH$_3$CO—and Et=CH$_3$CH$_2$—. If necessary, the reaction time is prolonged after the further addition of 25 mg of Pd/C. When the reaction is almost complete, the mixture is filtered through Celite$^R$ and rinsed rapidly with dry ethyl acetate. The filtrate is evaporated and the oil obtained is chromatographed on a column of Merck$^R$ 7734a silica equilibrated with a hexane/10% ethyl acetate mixture. The eluant is progressively enriched in ethyl acetate. The compound is eluted by a mixture containing 30% of ethyl acetate and checked on TLC. The desired product (22) is obtained in the form of leaflets: m=2.135 g; yield: 79%.

c) Cyanoethyl (1-ethoxy 2,3,4,6-tetra-O-benzoyl D-mannosyl) phosphate (23).

The barium salt of the cyanoethyl phosphate is first exchanged for the pyridinium salt. For this purpose, 2.6 g of this barium salt (8.043 mmoles) is added to 15 ml of water with vigorous stirring and Dowex 50 WX8 H$^{+R}$ resin is added until the salt completely dissolves. Stirring is continued for a further hour then the mixture is passed through a column of Dowex 50 WX8 H$^{+R}$ and the product is collected directly in pyridine. Elution is performed with water and collection is continued for as long as the pH of the eluate remains acid.

The eluate is then evaporated to dryness and the oil obtained is coevaporated 3 times with pyridine.

2.053 g (3.179 mmoles) of the sugar (22) are then added and coevaporation with anhydrous pyridine is again carried out 3 times. Finally, about 40 ml of anhydrous pyridine and 20 ml of distilled trichloroacetonitrile are added. The mixture is placed under nitrogen and heated at 70° C. with stirring for about 14 hours. An orange-coloured solution is obtained which is checked by means of TLC.

Rf=0 (AcOEt: hexane 2/1); Rf=0.72 (CH$_2$Cl$_2$: CH$_3$OH: H$_2$O 13/5/1).

The mixture is evaporated to dryness, the residue is taken up in a minimum of dichloromethane and precipitated by means of petroleum ether. The product is purified on a column of Merck$^R$ 7734 silica equilibrated with a 1/1 mixture of hexane: ethyl acetate which is progressively enriched to give pure ethyl acetate as eluant.

After evaporation, the desired product (23) is obtained in the form of a white powder: m=1.809 g; yield=67%.

d) Condensation with AZT (4) and preparation of 1-ethoxy 2,3,4,6-tetra-O-benzoyl D-mannosyl 5'-(3'azido)thymidinyl phosphate (24)

100 mg (0.375 mmole) of 3'-azido thymidine and 540 mg (0.375×1.7 mmoles) of benzoylated mannose (23) are coevaporated 3 times with anhydrous pyridine. About 10 ml of anhydrous pyridine and 285 mg (0.375×2 mmoles) of 2,4,6-triisopropyl benzenesulfonyl 3-nitro 1,2,4-triazole (TPSNT) are then added. The reaction is allowed to proceed at room temperature in a tightly stoppered flask and after one hour a check is made by means of TLC. If any starting material remains, TPSNT is added and reaction is allowed to proceed and checked by means of TLC. The mixture is then diluted with dichloromethane, washed with saturated sodium bicarbonate, water and then the organic phase is evaporated to dryness after drying over sodium sulfate. The residue is taken up in a minimum of dichloromethane and the product is precipitated by means of petroleum ether. The gum obtained is chromatographed on a column of Merck$^R$ 7734 silica equilibrated with dichloromethane and eluted with pure CH$_2$Cl$_2$. The product is then eluted by means of a CH$_2$Cl$_2$/1% methanol mixture.

The phosphodiester (22) is obtained in the form of a beige powder: m=198 mg; yield=52%; Rf=0.40 (CH$_2$Cl$_2$ 10% CH$_3$OH ).

e) Removal of the benzoyl and cyanoethyl groups and formation of 1ethoxy D-mannosyl 5'-(3'-azido) thymidinyl phosphate(25)

The 198 mg (0.194 mmole) of (24) previously obtained are dissolved in 20 ml of 1% sodium methylate in methanol.

The solution is stirred for 10 min. and a check is made by TLC that no starting material remains. The solution is neutralized by Dowex 50 WX8 H$^{+R}$ filtered and evaporated to dryness. The product obtained is scratched in the presence of ethyl ether in order to remove the benzoate obtained. The residue is dissolved in water and passed through a column of C18$^R$ eluted with water. The fractions are detected at 254 nm and checked by means of TLC. After lyophilization, the deprotected phosphodiester (25) is obtained in the form of a white powder: m=78 mg; yield=73%; Rf=0.529 (isopropanol: NH$_4$OH: H$_2$O 7/1/2).

f) Exchange to the tetrabutylammonium salt (26) or CT 7624

A column of Dowex 50 WX8 H$^{+R}$ resin in the tetrabutylammonium form is prepared.

The 78 mg of phosphodiester (25) is passed through this column by eluting with water. The fractions absorbing at 254 nm are collected and lyophilized: m=100 mg; yield=89%; Rf=unchanged; mass FAB$^-$=552 (m-1); HPLC: retention time=8.475 mn (5/25).

g) Preparation of the phosphotriester (27), namely 1-ethoxy D-mannosyl hexadecyl 5'-(3'-azido) thymidinyl phosphate (CT 7625)

70 mg (0.088 mmole) of the phosphodiester (26) and 0.498 ml (0.088×18 mmoles) of 1-iodohexadecane (8)

are coevaporated with anhydrous acetonitrile. 10 ml of anhydrous acetonitrile are then added and the mixture is heated at 80° C. for 16 to 20 h with stirring. A check is then made by means of TLC that no starting material remains. The mixture is evaporated to dryness and passed through a column of Merck$^R$ 7734 silica. The column is eluted with pure dichloromethane in order to remove the excess iodohexadecane. The eluant is then progressively enriched in methanol. The desired compound is eluted by means of a mixture containing 6% methanol. It is obtained in the form of a white powder: m=47 mg; yield=69%; Rf=0.692 (isopropanal: NH$_4$OH: H$_2$O 7/1/2); mass FAB$^-$=776 (m-1); HPLC: retention time of 2 peaks=14.091 mn, 14.5 mn (50/95); NMR (DMSO-d$_6$): CH$_3$ chain (0.85), (CH$_2$)n (1.25), CH$_2$—CH$_2$—OP (1.59), CH$_2$—CH$_2$—OP (4.00); mannose αH$_1$(4.69), H$_2$(3.63), H$_3$(3.48), H$_4$(3.35), H$_5$(3 42), H$_{6,6'}$(3.50); nucleotide H$_6$(7.46), CH$_3$(1.80), H$_1$'(6.13), H$_2'$,$_2''$(2.40), H$_3'$(4.46), H$_4$(4.02), H$_5'$,$_5''$(4.19); CH$_2$—CH$_2$—OP (3.59 and 3.79), CH$_2$—CH$_2$—OP(4.18).

EXAMPLE 5

Preparation of ddT Derivatives of Formula

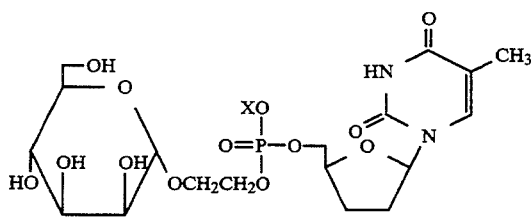

The procedure is that described in example 4.

The condensation step d) is carried out starting from 100 mg of ddT (9) (0.442 mmole) and 600 mg (0.442×1.59 excess) of phosphate (28) condensed in anhydrous pyridine in the presence of 336 mg of TPSNT (0.442×2 mmoles). After purification on a column of silica 245 mg of protected phosphodiester (29) are obtained; yield=56%; Rf=0.437 (CH$_2$Cl$_2$: CH$_3$OH: H$_2$O 13/5/1).

The debenzoylation and decyanoethylation step e) is carried out starting from the 245 mg of (29) treated with 25 ml of 1% sodium methylate. After purification, 98 mg of phosphodiester (30) are obtained in the form of the pyridinium salt; yield=70%; Rf=0.605 (isopropanol: NH$_4$OH: H$_2$O 7/1/2).

In step f), the pyridinium salt is exchanged for the tetrabutylammonium salt. 113 mg of phosphodiester (31) are obtained in the form of the tetrabutylammonium salt CT 7622: yield=86%; Rf=unchanged; mass FAB$^-$=511 (m-1); HPLC: retention time=5.348 mn (5/25).

The phosphotriester (32) is obtained according to step g) by treating 83 mg (0.11 mmole) of the diester (31) with 0.633 ml (0.11×18 mmoles) of 1-iodohexadecane (8) in dry acetonitrile. After passage through a column 54 mg of the phosphotriester CT 7623 are obtained: yield=67%; Rf=0.69 (isopropanol: NH$_4$OH: H$_2$O 7/1/2)=0.78 (CH$_2$Cl$_2$: CH$_3$OH: H$_2$O 13/5/1); mass FAB$^+$=759.4 (m+Na$^+$); HPLC: retention time 2 peaks=13.597 min. 14.028 min. (50/95).

EXAMPLE 6

Preparation of dFU Derivatives of Formula

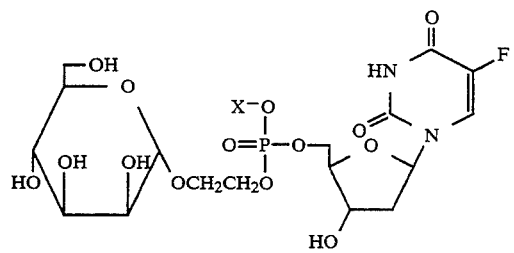

The procedure is that indicated in example 4.

The condensation step is carried out starting from 100 mg of 2'deoxy-5-fluoro uridine (14) (0.406 mmole) and 588 mg (0.406×17 excess) of phosphate (23) condensed in anhydrous pyridine in the presence of 309 mg of TPSNT (0.406×2 mmoles). After chromatography 141 mg of protected phosphodiester (33) are obtained in the form of the pyridinium salt: yield=35%; Rf=0.46 (CH$_2$Cl$_2$: CH$_3$OH: H$_2$O 13/5/1).

The debenzoylation and decyanoethylation are carried out according to step e) as indicated in example 4 starting from the 141 mg of (33). 53 mg of deprotected phosphodiester (34) are obtained in the form of the pyridinium salt by treatment with 15 ml of 1% sodium methylate: yield=71%; Rf=0.52 (isopropanol: NH$_4$OH: H$_2$O 7/1/2).

The exchange into the tetrabutylammonium salt according to step f) leads to 67 mg of product (35) CT 7387: yield=87%; Rf=unchanged; mass FAB$^-$=531 (m-1); HPLC: retention time=10.574 (0/25).

The phosphotriester (35) is obtained by treatment of 55 mg (0.067 mmole) of the diester (34) in acetonitrile with 0.38 ml (0.067×18 mmoles) of 1-iodohexadecane (8) in the usual manner: m=35.3 mg CT 7388; yield=69.5%; Rf=0.66 (isopropanol: NH$_4$OH: H$_2$O 7/1/2); Rf=0.77 (CH$_2$Cl$_2$: CH$_3$OH: H$_2$O 13/5/1); mass FAB$^+$=779.8 (m+Na$^+$); HPLC: retention time 2 peaks=10.414 min. 10.834 min. (50/95); NMR (DMSO-d$_6$): CH$_3$ chain (0.89), (CH$_2$)$_n$ (1.25), CH$_2$—CH$_2$—OP (1.60), CH$_2$—CH$_2$—OP (3.95); mannose α H$_1$(4.67), H$_2$(3.64), H$_3$(3.46), H$_4$(3.32), H$_5$, H$_{6,6'}$(3.45); nucleotide H$_6$(7.90 and 7.88 45/55), H$_1'$(6.17) H$_2'$,$_2''$(2.15), H$_3'$(4.24), H$_4'$(3.94), H$_5'$,$_5''$(4.00); CH$_2$—CH$_2$—OP (3.61 and 3.77), CH$_2$—CH$_2$—OP (4.11).

EXAMPLE 7

Study of the Anti-HIV Effect of the Derivatives of the Invention

The results reported below relate to assays making it possible to monitor:
the inhibition of the cytopathogenic effect (CPE) of the HIV virus towards a continuous line of T4 lymphocytes by colorimetric assay with MTT, a technique developed in the laboratory of Viral Oncology (O. Schwartz et al., 1988, AIDS Research and Human Retrovirus, vol. 4, No. 6, p. 441);
the inhibition of vital replication by microassay of the enzymatic activity of the viral reverse transcriptase.

Materials

Cells

The line CEM-C113 (a clone particularly sensitive to the CPE of the virus) was employed.

Virus

The isolate LAV1-BRU deposited with the Collection des Cultures Nationales de Microorganismes (CNCM) of the Pasteur Institute on 15 Jul. 1983 under the No. I-232.

The viral solution used, obtained from a supernatant of CEM producing cells, was titred before use.

Compounds Tested

The compounds which are available in the form of a powder are dissolved to give a 5 mM solution in water or DMSO (dimethylsulfoxide) depending on their solubilities. These stock solutions are stored at $+4°$ C. They are then diluted in RPMI medium in order to obtain the desired assay concentrations (the final concentrations assayed vary from 25 $\mu$M to 0.2 $\mu$M). For comparison, AZT, dideoxycytidine (ddC) and dideoxythymidine (ddT) were also studied under the same conditions.

Study of the Inhibition of the CPE of the HIV Virus Toward a Continuous Line of T4 Lymphocytes by Colorimetric Assay with MTT a) Assay of the CPE of the virus and the cytotoxicity of the compounds tested The colorimetric assay makes use of MTT(3-(4,5-dimethyl-thiazol-2-yl) 2,5-diphenyltetrazolium bromide), a yellow substrate which leads to the formation of a product with a dark blue colour when it is incubated with living cells. The intensity of the colour formed is directly proportional to the concentration of living cells present in the sample studied.

The protocol employed which is described in AIDS Research and Human Retrovirus by O. Schwarz et al (above reference) (1) may be briefly summarized here:
  100 $\mu$l of CEM-CL13 cells (3.104$^4$/ml) were distributed on microplates;
  50 $\mu$l of different dilutions of the compounds to be tested are added.
  6 wells are prepared for each concentration:
  3 for the study of the cytotoxicity of the compounds;
  3 for the study of the inhibitory properties towards viral production.

Incubation for 2 h at 37° C. in an incubator under 5% $CO_2$ is followed by the addition of:
  either 100 $\mu$l of culture medium (cytotoxicity study);
  or 100 $\mu$l of viral solution with a multiplicity of infection of 0.008 (study of the antiviral effect).

After 7 days of culture, 50 $\mu$l of supernatant are taken for the assay of reverse transcriptase activity (RTA). The cells are then suspended by shaking. 100 $\mu$l of the cellular suspension are taken in order to perform the MTT test. To the remaining cells are added 150 $\mu$l of fresh medium containing the drugs at the desired concentrations. The cells are passed in this way every 3 to 4 days. At each passage the reverse transcriptase activity and the CPE are assayed.

b) MTT assay

The MTT is dissolved in PBS at a concentration of 5 $\mu$g/ml and filtered. Ten $\mu$l of this stock solution are added to microwells containing 100 $\mu$l samples of the cells to be tested, The plates are incubated at 37° C. for 4 hours, The supernatants are then carefully removed and 150 $\mu$l of 0.04 N HCl in isopropanol are added to dissolve the blue crystals formed. The plates are then read in a microplate reader (Biotek) at a wavelength of 540 nm, Study of the cytotoxicity of the compounds tested Cells treated with the drugs but not infected with HIV are used to determine the toxicity of the drugs.

The control cells (without virus and without drug) define 100% absorbance during the MTT assay, The cytotoxic dose 50 (CD50) is defined as being that leading to a diminution of absorbance of 50% with respect to the controls.

Study of the protection provided by the compounds tested

The anti-HIV activity is determined by using the following formula:

$$\text{Protection} = \frac{\text{O.D. (drug + HIV)} - \text{O.D. (HIV)}}{\text{O.D. (drug)} - \text{O.D. (HIV)}} \times 100\%$$

where O.D. (drug +HIV) corresponds to the absorbance at 540 nm of the cells treated with the drugs and infected by the virus.

O.D. (HIV) corresponds to the absorbance at 540 nm of the cells infected by the virus and untreated with the drugs.

O.D. (drug) corresponds to the absorbance at 540 nm of the uninfected cells treated with the drugs.

The protecting dose 50 (ED50) is that leading to a 50% protection against the CPE.

Determination of the selectivity index

The higher the difference between the CD50 and the ED50, the more useful will be the product. This difference is quantified by the selectivity index (the CD50/ED50 ratio).

In the tables 1a and 1b below are reported the results obtained after 7 to 22 days of culture relating to the protective effect and the protection indices (CD50/ED50), respectively:
  of mannosylated derivatives of AZT according to the invention (phosphodiesters 7624 and 7626, phosphotriesters 7625 and 7627).
  of AZT, ddC and ddT.

TABLE Ia

| COMPOUND | DAYS OF CULTURE | | | | | | | |
|---|---|---|---|---|---|---|---|---|
| | D7 | | D11 | | D19 | | D22 | |
| | CD50 | ED50 | CD50 | ED50 | CD50 | ED50 | CD50 | ED50 |
| 7624 | 25 | <0.2 | >25 | <0.2 | >25 | <0.2 | >25 | 0.8 |
| 7625 | 20 | <0.2 | 28 | 1 | 3.4 | >1 | 24 | >1 |
| 7626 | >25 | <0.2 | >25 | 0.2 | 24 | 0.2 | 24 | 0.6 |
| 7627 | 2.6 | <0.2 | 2.6 | 0.3 | 2.5 | 0.5 | 25 | 0.4 |
| AZT | >25 | <0.2 | 23 | <0.2 | >25 | <0.2 | 22 | 0.45 |
| ddC | 7 | <0.2 | 0.4 | — | <0.2 | — | <0.2 | — |
| ddT | >25 | <0.2 | <25 | 0.7 | >25 | 0.8 | >25 | >25 |

CD50 = cytotoxic dose 50% (on uM)
ED50 = protective dose 50% (on uM)
— : no protective effect detected

TABLE Ib

| COMPOUND | PROTECTION INDICES (P.I.) | | | |
|---|---|---|---|---|
| | D7 | D11 | D19 | D22 |
| 7624 | >125 | >125 | >125 | >42 |
| 7625 | >100 | 28 | <3,4 | <3,4 |
| 7626 | >125 | >125 | >120 | >40 |
| 7627 | >13 | 9 | 5 | 6 |
| AZT | >125 | >125 | >125 | 49 |
| ddC | >35 | 0 | 0 | 0 |

It is observed that AZT possesses a selectivity index higher than 50 after 22 days of culture. Advantageously, the products 7624 and 7626 possess selectivity indices comparable to AZT.

Study of the Inhibition of Viral Replication by Microassay of the Enzymatic Activity of the Viral Reverse Transcriptase The reverse transcriptase activity is determined directly on 50 μl of culture supernatant according to the following method: the enzymatic activities are measured after addition of 10 μl of a reaction mixture containing 0.1% Triton X100, 0.1 M KCl, 10 mM DTT to which is added 40 μl of a reaction mixture containing 5 mM EGTA in 0.5 M of Tris-HCl buffer, 0.5 M $MgCl_2$ 1 $\mu Ci^3 HTTP$, 0.5 g/l poly (rA) oligo (dT). After incubation for one hour at 37° C., the reaction is stopped by the addition of a 120 mM solution of $Na_4P_2O_7$ in 60% TCA, then left at 4° C. for 15 minutes. The material precipitated is recovered by means of a Skatron filtration system after several washings with 12 mM $Na_4P_2O_7$ in 5% TCA. The filters are dried and the radioactivity is measured with the aid of a β scintillation counter (Packard).

Table 2 below presents the results of the assay of reverse transcriptase activity in the culture supernatants after 7 to 26 days.

Study of the Transmembrane Transport of the AZT Compounds According to the Invention on Model Unilamellar Vesicles by Means of $^{31}P$ NMR and Assay of the AZT Found in the Brain of Mice After Ingestion of These Compounds a) $^{31}$P-NMR study of the interactions between the phosphotriesters and model membranes The protocol followed is that described in JACS 1989 111, 4270. This study shows that CT 7627 interacts only with the external lipid layer of the unilamellar vesicles whereas CT 7625 is found in the intravesicular aqueous phase. This latter compound appears to be the best lipophilic carrier of AZT of all of the phosphotriester synthesized.

b) HPLC assay of AZT in the brain of mice

The assays are conducted on the Swiss mouse. The compounds assayed are AZT (control), the 6-mannosyl CT 7626 and 1-mannosyl CT 7624 phosphodiesters and the corresponding phosphotriesters CT 7627 and CT 7625.

The animals are given 25 mg/kg of AZT or of phosphodiester and triester (about 500 μg/mouse) orally. The compounds are dissolved in distilled water (or suspended in distilled water) before being administered by gavage; the assays are performed by administering each compound to 3 mice. The control consists of 3 mice receiving the equivalent of the vehicle, i.e. the same volume of distilled water as the treated mice. The brains are removed 1 hour after garage, homogenized in an acetonitrile-water (3/1) mixture, centrifuged and the supernatant is taken for the HPLC assay.

The supernatant (½) is assayed by means of HPLC on a C18 silica column; quantification is done by internal calibration by the addition of a defined amount of the compounds to be assayed (AZT, phosphodiester and phosphotriester) to the other half of the supernatant. In a preliminary trial, favourable experimental conditions for the assays of the different compounds by HPLC are determined.

TABLE II

| ANTI-HIV EFFECT | | CEM CELLS | | | | | |
|---|---|---|---|---|---|---|---|
| | | DAYS OF CULTURE | | | | | |
| COMPOUND | | D7 | D11 | D18 | D19 | D22 | D26 |
| 7624 | 25 uM | 1204 | 372 | 304 | 2100 | 500 | 1700 |
| | 5 uM | 1670 | 1003 | 852 | 2700 | 5500 | 42000 |
| | 1 uM | 2800 | 1900 | 2200 | 12000 | 26000 | 55000 |
| | 0.2 uM | 4400 | 2800 | 2600 | 24000 | 27000 | 70000 |
| 7625 | 25 uM | | | | | | |
| | 5 uM | | | | | | |
| | 1 uM | 6000 | 6000 | 5500 | 47000 | 48000 | 64000 |
| | 0.2 uM | 3900 | 2900 | 2400 | 25000 | 52000 | 61000 |
| 7626 | 25 uM | 1100 | 700 | 900 | 2200 | 900 | 900 |
| | 5 uM | 1500 | 1000 | 1300 | 8000 | 12000 | 100000 |
| | 1 uM | 2700 | 1300 | 1200 | 5000 | 15000 | 50000 |
| | 0.2 uM | 3400 | 3000 | 1700 | 12000 | 27000 | 85000 |
| 7627 | 25 uM | | | | | | |
| | 5 uM | | | | | | |
| | 1 uM | 2000 | 1100 | 500 | 1400 | 3900 | 20000 |
| | 0.2 uM | 4000 | 4700 | 1700 | 11000 | 24000 | 73000 |
| AZT | 25 uM | 600 | 550 | 400 | 300 | 500 | 900 |
| | 5 uM | 900 | 800 | 500 | 700 | 500 | 1300 |
| | 1 uM | 100 | 750 | 600 | 650 | 1700 | 12000 |
| | 0.2 uM | 1500 | 1600 | 1100 | 1800 | 6400 | 28000 |
| ddT | 25 uM | 2500 | 1000 | 800 | 7000 | 4000 | 5000 |
| | 5 uM | 5000 | 2000 | 1400 | 5000 | 2100 | 5000 |
| | 1 uM | 3000 | 1500 | 750 | 1200 | 350 | 600 |
| untreated control | | 21000 | 57000 | 19000 | 13000 | 5000 | 15000 |
| uninfected cell control | | 600 | 800 | 500 | 1300 | 600 | 700 |

In the table which follows, each line corresponds to an assay series. The first and last columns summarize the results and give the amounts of AZT (in μmol) given by ingestion of aqueous solutions to mice and the total amounts of AZT (in nanomol) found per gram of brain: for example, the administration of 1.87 μmol of AZT (500 μg) per mouse leads to 2.7 nanomol of AZT being found per gram of brain.

These results are to be compared with those described in Torrence P. F. et al., FEBS Letters, 1988, 233, 135-140 with a dihydropyridinyl derivative of AZT designed as a vector directed towards the central nervous system: the intravenous injection of 20 mg/kg of the compound HPAZT (1 μmol of AZT) dissolved in DMSO (0.1 to 0.2 ml) gives a concentration of 2.6 to 7.7 nanomol of AZT equivalent per gram of brain. In view of the fact that the bioavailability of the oral doses of AZT is of the order of 60% (in man) (Yarchoan R. et al., The Lancet, 1986, 576-580), the phosphodiesters and triesters of AZT (CT 7624-7627) appear to be particularly efficacious lipophilic derivatives of AZT compared with the AZT derivatives synthesized up to the present: the oral administration of these compounds leads to practically 3 times more AZT being found in the brain after the ingestion of a 2 to 3 fold lower dose of AZT.

| | | QUANTITY DETECTED BY HPLC PER GRAM OF BRAIN | | | | |
|---|---|---|---|---|---|---|
| | | | | Compound identified | | |
| AZT equivalent (micromol) per mouse | Assay | Compound tested | AZT μg | Phosphodiester μg | Phosphotriester μg | Total as AZT equivalent (nanomol) |
| 1.87 | 1 | AZT (M.267) | 0.66, 0.37, 0.93, 0.92 } 0.72 | | | 2.7 |
| 0.94 | 2 | Glucosyl-6 diester CT 6715 (M. 532) | 1.06, 0.42, 0.96 } 0.81 | ?, 2.51, 3.15 } 2.83 | | 8.4 |
| 0.68 | 3 | Glucosyl-6 triester CT 6651 (M. 733) | 5.92, 0.47, 1.02 } 0.75 | ?, 3.27, 6.21 } 4.74 | 0, 0, 0 | 11.7 |
| 0.94 | 4 | Mannosyl-6 diester CT 7626 (M.532) | 1.34, 0.89 } 1.12 | ?, 2.05 | | 8.0 |
| 0.68 | 5 | Mannosyl-6 triester CT 7627 (M. 733) | 0.90, 0.54 } 0.72 | ?, 2.05 | 0, 0 | 6.6 |
| 0.90 | 6 | Mannosyl-1 diester CT 7624 (M. 552) | 1.77, 0.89 } 1.33 | 0.92, 3.70 } 2.31 | | 9.2 |
| 0.64 | 7 | Mannosyl-1 triester CT 7625 (M. 777) | 2.14, 0.79 } 1.47 | 1.17, 3.51 } 2.34 | 0, 0 | 9.7 |

We claim:

1. A glycosylated nucleotide of the formula:

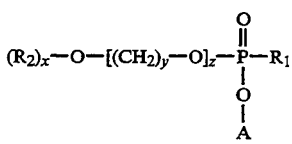

wherein:

R₁ is a nucleoside derivative selected from the group consisting of 3'-azidothymidine (AZT); 2',3'-dideoxythymidine (ddT); and 2'-deoxy-5-fluorouridine (dFU);

R₂ is a hexose or pentose sugar, with the exception of glucose when x is 1;

A is a hydrogen atom or an alkyl or alkoxy chain containing from 5 to 20 carbon atoms, said alkyl or alkoxy chain having at its extremity a group selected from the group consisting of a hydrogen atom and an NR'R" group, wherein R' and R" represent hydrogen or an alkyl group of 1 to 4 carbon atoms;

x is a number from 1 to 12;

y is a number from 1 to 4; and z is 0 or 1; and further wherein:

attachment of said hexose sugar is at position 1 or position 6 of said hexose sugar, and attachment of said pentose sugar is at position 1 or position 5 of said pentose sugar.

2. The glycosylated nucleotide as claimed in claim 1, wherein R₂ is selected from the group consisting of mannose, galactose, fructose, fucose, aminohexose, 2-deoxy glucose, arabinose, xylose, ribose, and 2-deoxy ribose.

3. A glycosylated nucleotide of the formula:

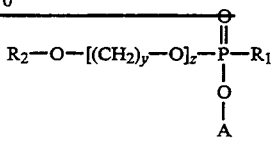

wherein:

R₁ is a nucleoside derivative selected from the group consisting of 3'-azidothymidine (AZT); 2',3'-dideoxythymidine (ddT); and 2'-deoxy-5-fluorouridine (dFU);

R₂ is a mannose;

A is a hydrogen atom or an alkyl or alkoxy chain containing from 5 to 20 carbon atoms, said alkyl or alkoxy chain having at its extremity a group selected from the group consisting of a hydrogen atom and an NR'R" group, wherein R' and R" represent hydrogen or an alkyl group of 1 to 4 carbon atoms;

y is a number from 1 to 4; and z is 0 or 1; and further wherein:

attachment of said mannose is at position 1 or position 6 of said mannose.

4. The glycosylated nucleotide as claimed in claim 3, wherein said glycosylated nucleotides are of the formula:

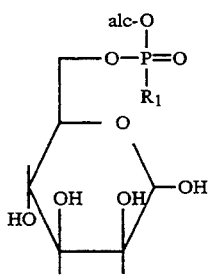

wherein:

alc is an alkyl or alkoxy chain containing from 5 to 20 carbon atoms, said alkyl or alkoxy chain having at its extremity a group selected from the group consisting of a hydrogen atom and an NR'R" group, wherein R' and R" represent hydrogen or an alkyl group of 1 to 4 carbon atoms; and $R_1$ is a nucleoside derivative selected from the group consisting of 3'-azidothymidine (AZT); 2',3'-dideoxythymidine (ddT); and 2'-deoxy-5-fluorouridine (dFU).

5. The glycosylated nucleotide as claimed in claim 4, wherein said glycosylated nucleotide is 6-D-mannosyl hexadecyl 5'-(3'-azido)-thymidinyl phosphate (CT 7627).

6. The glycosylated nucleotide as claimed in claim 4, wherein said glycosylated nucleotide is 6-D-mannosyl hexadecyl 5',2',3'-dideoxy thymidinyl phosphate (CT 7390).

7. The glycosylated nucleotide as claimed in claim 4, wherein said glycosylated nucleotide is 6-D-mannosyl hexadecyl 5'-(2'-deoxy)-5-fluorouridinyl phosphate (CT 7325).

8. The glycosylated nucleotide as claimed in claim 3, wherein said glycosylated nucleotide is of the formula:

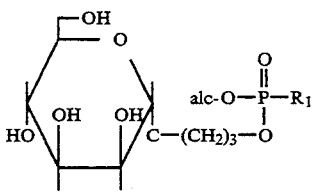

wherein:

alc is an alkyl or alkoxy chain containing 5 to 20 carbon atoms, said alkyl or alkoxy chain having at its extremity a group selected from the group consisting of a hydrogen atom and an NR'R" group, wherein R' and R" represent hydrogen or an alkyl group Of 1 to 4 carbon atoms;

$R_1$ is a nucleoside derivative selected from the group consisting of 3'-azidothymidine (AZT); 2',3'-dideoxythymidine (ddT); and 2'-deoxy-5-fluorouridine (dFU); and y is a number from 1 to 4.

9. The glycosylated nucleotide as claimed in claim 8, wherein said glycosylated nucleotide is 1-ethoxy-D-mannosyl hexadecyl 5'-(3'-azido) thymidinyl phosphate (CT 7625).

10. The glycosylated nucleotide as claimed in claim 8, wherein said glycosylated nucleotide is 1-ethoxy-D-mannosyl hexadecyl 5'-(2'-3'-dideoxy) thymidinyl phosphate (CT 7623).

11. The glycosylated nucleotide as claimed in claim 8, wherein said glycosylated nucleotide is 1-ethoxy-D-mannosyl hexadecyl 5'-(2'-deoxy-5-fluorouridinyl) phosphate (CT 7388).

12. The glycosylated nucleotide as claimed in claim 3, wherein said glycosylated nucleotide is of the formula:

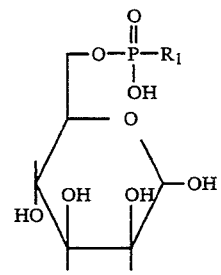

wherein:

$R_1$ is a nucleoside derivative selected from the group consisting of 3'-azidothymidine (AZT); 2',3'-dideoxythymidine (ddT); and 2'-deoxy-5-fluorouridine (dFU).

13. The glycosylated nucleotide as claimed in claim 3, wherein said glycosylated nucleotide is of the formula:

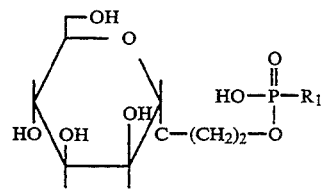

wherein:

$R_1$ is a nucleoside derivative selected from the group consisting of 3'-azidothymidine (AZT); 2',3'-dideoxythymidine (ddT); and 2'-deoxy-5-fluorouridine (dFU); and y is a number from 1 to 4.

14. A pharmaceutical composition comprising a glycosylated nucleotide as claimed in claim 3 in admixture with a pharmaceutically acceptable vehicle.

15. Process for the preparation of a glycosylated nucleotide comprising:

(a) providing a glycoside derivative of the formula:

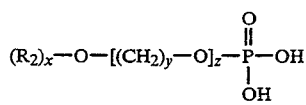

wherein:

$R_2$ is a hexose or pentose sugar, with the exception of glucose when x is 1, and where all hydroxyl groups of said sugar are blocked by protecting groups;

x is a number from 1 to 12;
y is a number from 1 to 4; and
z is 0 or 1;

(b) providing a nucleoside derivative selected from the group consisting of 3'-azidothymidine (AZT), 2',3'-dideoxythymidine (ddT); and 2'-deoxy-5-fluorouridine (dFU);

(c) condensing said glycoside derivative with said nucleoside derivative to form a phosphodiester of the formula:

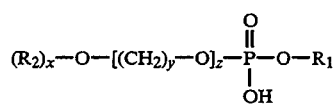

wherein:
$R_1$ is selected from the group consisting of 3'-azidothymidine (AZT); 2',3'-dideoxythymidine (ddT); and 2'-deoxy-5-fluorouridine (dFU);

$R_2$ is a hexose or pentose sugar, with the exception of glucose when x is 1, and where all hydroxyl groups of said sugar are blocked by protecting groups;

x is a number from 1 to 12;
y is a number from 1 to 4; and
z is 0 or 1; and (d) removing said protecting groups from hydroxyl groups of said sugar.

16. Process for the preparation of the glycosylated nucleotide as claimed in claim 15, wherein said process further comprises:

reacting the phosphodiester with a reagent of the formula B-alc, where B is a group capable of reacting with a —OH group attached to phosphorus, and the alc group is an alkyl or alkoxy chain containing from 5 to 20 carbon atoms, said alkyl or alkoxy chain having at its extremity a group selected from the group consisting of a hydrogen atom and an NR'R'' group, wherein R' and R'' represent hydrogen or an alkyl group of 1 to 4 carbon atoms, to form a phosphotriester of the formula:

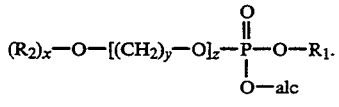

17. Process for the preparation of a glycosylated nucleotide comprising:
(a) providing a glycoside derivative of the formula:

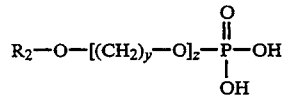

wherein:
$R_2$ is a mannose sugar in which all hydroxyl groups of the mannose sugar are blocked by protecting groups;
y is a number from 1 to 4; and
z is 0 or 1;

(b) providing a nucleoside derivative selected from the group consisting of 3'-azidothymidine (AZT); 2',3'-dideoxythymidine (ddT); and 2'-deoxy-5-fluorouridine (dFU);

(c) condensing said glycoside derivative with said nucleotide derivative to form a phosphodiester of the formula:

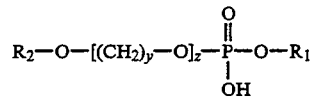

wherein:
$R_1$ is selected from the group consisting of 3'-azidothymidine (AZT); 2',3'-dideoxythymidine (ddT); and 2'-deoxy-5-fluorouridine (dFU);

$R_2$ is a mannose sugar in which all hydroxyl groups of the mannose sugar are blocked by protecting groups;
y is a number from 1 to 4; and
z is 0 or 1; and (d) removing said protecting groups from hydroxyl groups of said mannose sugar.

18. Process for the preparation of the glycosylated nucleotide as claimed in claim 17, wherein said process further comprises:

reacting the phosphodiester with a reagent of the formula B-alc, where B is a group capable of reacting with a —OH group attached to phosphorus, and alc is alkyl or alkoxy chain containing from 5 to 20 carbon atoms, said alkyl or alkoxy chain having at its extremity a group selected from the group consisting of a hydrogen atom and an NR'R'' group, wherein R' and R'' represent hydrogen or an alkyl group of 1 to 4 carbon atoms, to form a phosphotriester of the formula:

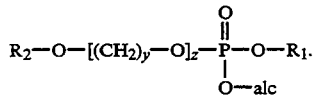

* * * * *

UNITED STATES PATENT AND TRADEMARK OFFICE
CERTIFICATE OF CORRECTION

PATENT NO. : 5,358,937

DATED : October 25, 1994

INVENTOR(S) : DINH et al.

It is certified that error appears in the above-identified patent and that said Letters Patent is hereby corrected as shown below:

On the title page, item [57] Abstract last line, "anti-vital" should read --anti-viral--.

IN THE CLAIMS:

Claim 3, column 20, formula "crashes" into base rule of unnumbered table, above.

Column 21:

Claim 4, line 2, "glycosylated nucleotides are" should read --glycosylated nucleotide is--.

Claim 8, col. 21, in the formula at line 56, "C-$(CH_2)_3$" should read --O-$(CH_2)_y$--.

Claim 8, col. 21, line 66, "Of" should read --of--.

UNITED STATES PATENT AND TRADEMARK OFFICE
CERTIFICATE OF CORRECTION

PATENT NO. : 5,358,937
DATED : October 25, 1994
INVENTOR(S) : DINH et al

It is certified that error appears in the above-indentified patent and that said Letters Patent is hereby corrected as shown below:

Claim 13, col. 222, in the formula at line 46, "$C-(CH_2)_2$" should read --$O-(CH_2)y$--.

Signed and Sealed this

Fourteenth Day of February, 1995

Attest:

BRUCE LEHMAN

Attesting Officer     Commissioner of Patents and Trademarks